United States Patent
Daeschel et al.

(12) 
(10) Patent No.: US 6,316,034 B1
(45) Date of Patent: *Nov. 13, 2001

(54) METHODS FOR REDUCING SPOILAGE IN BREWERY PRODUCTS

(75) Inventors: Mark A. Daeschel, Philomath; Linda D. Bruslind, Lebanon, both of OR (US)

(73) Assignee: The State of Oregon acting by and through the State Board of Higher Education on behalf of Oregon State University, Corvallis, OR (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/231,287

(22) Filed: Jan. 15, 1999

Related U.S. Application Data (62) Division of application No. 08/906,266, filed on Aug. 5, 1997.

(51) Int. Cl.[7] .................................................. C12C 11/00
(52) U.S. Cl. .................. 426/16; 426/29; 426/61
(58) Field of Search ................... 426/12, 13, 16, 426/29, 61, 592

(56) References Cited

U.S. PATENT DOCUMENTS 5,458,876 * 10/1995 Monticello ..................... 424/94.61

FOREIGN PATENT DOCUMENTS

240054 * of 1986 (CZ).
46-3114 * of 1967 (JP).

OTHER PUBLICATIONS

Hardwick, W. A., Handbook of Brewing, Marcel Dekker, Inc., New York, 1994, pp. 193–194.*

Makki et al, Food Research International, 29 (7) pp. 635–645, 1996.*

Slovak Food Code Jun. 1996 Head III, Part 2, Annex 1, Additives and Technological Auxiliary Compounds in Foods, Part G, I.*

Henning et al., "New aspects for the application of nisin to food products based on the mode of action," *Int'l J. Food Microbiol.* 3:135–141 (1986).

Ogden, "Nisin: A bacteriocin with a potential use in brewing," *J. Inst. Brew.* 92:379–383 (1986).

Proctor and Cunningham, "The chemistry of lysozyme and its use as a food preservative and a pharmaceutical," *CRC Crit. Rev. Food Sci. Nutrition* 26:359–395 (1988).

Stadelman et al., Egg Science and Technology, 2nd Ed., AVI Publishing Co., Inc., Westport, Conn., 1977, pp. 74–77, and 190–195.

* cited by examiner

*Primary Examiner*—Curtis E. Sherrer
(74) *Attorney, Agent, or Firm*—Klarquist Sparkman, LLP (57) ABSTRACT

The growth of spoilage bacteria in yeast preparations and in fermentation products is inhibited by addition of lysozyme at various steps in the production process.

7 Claims, 9 Drawing Sheets

METHODS FOR REDUCING SPOILAGE IN BREWERY PRODUCTS

This is a division of application Ser. No. 08/906,266, filed Aug. 5, 1997.

BACKGROUND OF THE INVENTION

This invention relates to the use of lysozyme in the production of fermented beverages.

Contamination of malt beverages by spoilage bacteria is an ancient problem. Large brewers today commonly filter or heat malt beverages to eliminate spoilage bacteria.

Henning et al., *Int'l J. Food Microbiol.* 3:135–141, 1986, discusses the use of various antibiotics, including nisin, virginiamycin, erythromycin, oleandomycin, and flavomycin, as preservatives for fruit mashes and juices.

Ogden, *J. Inst. Brew.* 92:379–383, 1986, discusses the use of nisin to inhibit the growth of lactic acid bacteria (Lactobacillus) during beer production.

Proctor and Cunningham, "The chemistry of lysozyme and its use as a food preservative and a pharmaceutical," *CRC Crit. Rev. Food Sci. Nutrition* 26:359–395, 1988, reviews the use of lysozyme as a food preservative and a pharmaceutical.

There remains a need for effective methods to prevent contamination of malt beverages, wine, and other fermented beverages by spoilage bacteria during the production process without substantially affecting the quality of the final product.

SUMMARY OF THE INVENTION

Lysozyme is surprisingly effective in reducing spoilage of fermented products, such as malt beverages, that results from contamination by a spoilage bacterium. Lysozyme is added at a concentration that is effective to inhibit growth of a bacterium (an "effective concentration") at any of several steps in the process of producing the fermented product, including, but not limited to: addition to a yeast inoculum (e.g., to dried yeast prior to rehydration or to a fresh or rehydrated yeast preparation); addition to a wort prior to or during fermentation to produce a malt beverage; addition during filling operations; etc.

According to one embodiment of the invention related to a method of producing a malt beverage, lysozyme is added directly to yeast before addition of the yeast to a wort to commence fermentation. For example, dry lysozyme can be added to an active dried preparation of yeast prior to rehydration of the dried yeast. Alternatively, lysozyme (dry or in a suspension or solution) can be added to a hydrated yeast preparation. According to other embodiments of the invention, lysozyme is added (i) to the wort prior to or after adding a yeast inoculum to produce a "fermentation mixture" that is allowed to ferment to produce a malt beverage; or (ii) to the malt beverage prior to or at the time of the filling of a container (e.g., a cask or bottle). Additional compounds can also be added to enhance the effectiveness of lysozyme in inhibiting bacterial growth, e.g., chelating agents, butyl p-hydroxybenzoate, a p-hydroxy-benzoic ester, β-glycopyranose aerodehydrogenase, amino acids, hydrogen peroxide, organic acids, and mixtures thereof.

According to another embodiment of the invention, malt beverages are provided that comprise an effective concentration of lysozyme, including malt beverages made by the methods described above.

According to another embodiment of the invention, methods are provided for making fermented products. Such methods include (i) adding to a sample that includes a fermentable carbohydrate a yeast preparation that includes yeast and an amount of lysozyme that is effective to inhibit the growth of a bacterium in the yeast preparation, and (ii) providing conditions that are conducive to fermentation of the carbohydrate by the yeast. A compound can also be added, for example to the yeast preparation, to enhance the effectiveness of lysozyme in inhibiting bacterial growth. The yeast preparation can be further treated by acid washing the yeast, preferably prior to addition of lysozyme, in order to reduce the bacterial population of the yeast preparation. In one embodiment, the yeast preparation is a dried preparation that includes active dried yeast and a concentration of dried lysozyme (e.g., about 0.5% to about 2.0% dried lysozyme by weight) that is sufficient to effectively inhibit bacterial growth upon rehydration of the yeast preparation. Such dried yeast preparations can be rehydrated by the addition of an aqueous liquid prior to use.

The foregoing and other aspects of the invention will become more apparent from the following detailed description and accompanying drawings.

DETAILED DESCRIPTION OF THE PREFERRED EMBODIMENTS

Beer is subject to contamination by unwanted spoilage bacteria, including lactic acid bacteria, at any of several steps in the production process. Addition of lysozyme (N-acetylhexosaminodase) at one or more of these steps prevents growth of spoilage bacteria without negatively affecting the quality (e.g., color, taste, etc.) of the final product.

Lysozyme lyses bacterial cells by hydrolyzing the β(1–4) linkages between N-acetylmuramic acid and N-acetylglucosamine in the peptidoglycan of the bacterial cell wall. Because of the nature of their cell walls, Gram-positive bacteria are most susceptible to lysozyme.

Lysozyme is employed at a concentration that is effective to inhibit the growth of spoilage bacteria without having a significantly negative impact on the quality of the fermented product, preferably between about 5 ppm to about 2000 ppm. Lysozyme at 150 ppm in beer, for example, is high enough to inhibit sensitive bacteria and achieves good maintenance of activity over time with virtually no physical changes to the beer (e.g., turbidity and foam). For reference purposes, addition of a 125-gram package of lysozyme can be added to a 55-gallon barrel of beer gives a final concentration of 300 ppm.

Lysozyme can be added in a dry form or can be diluted prior to addition, e.g., with water, to ensure that the lysozyme dissolves completely.

Lysozyme can be used in combination with any compound that is conventionally used to increase the bacteriocidal effectiveness of lysozyme (or mixtures thereof), including, but not limited to: chelating agents (e.g., phytic acid), butyl p-hydroxybenzoate (POBB), p-hydroxy-benzoic esters, β-glycopyranose aerodehydrogenase, amino acids (e.g., glycine, threonine, or lysine), hydrogen peroxide, and organic acids such as citric acid or ascorbic acid. For example, citric acid or another chelating agent may be particularly useful for enhancing the effectiveness of lysozyme against Gram-negative spoilage bacteria by binding magnesium ions that are required for stability of the outer cell membrane.

The lysozyme may be added as a dried enzyme or as a suspension or solution in water or a conventional buffer that is compatible with lysozyme activity, e.g., tris (hydroxymethyl aminomethane (Tris) buffer. Such a solution or suspension can also include an osmotic stabilizer (e.g., polyethylene glycol).

Figure 1:
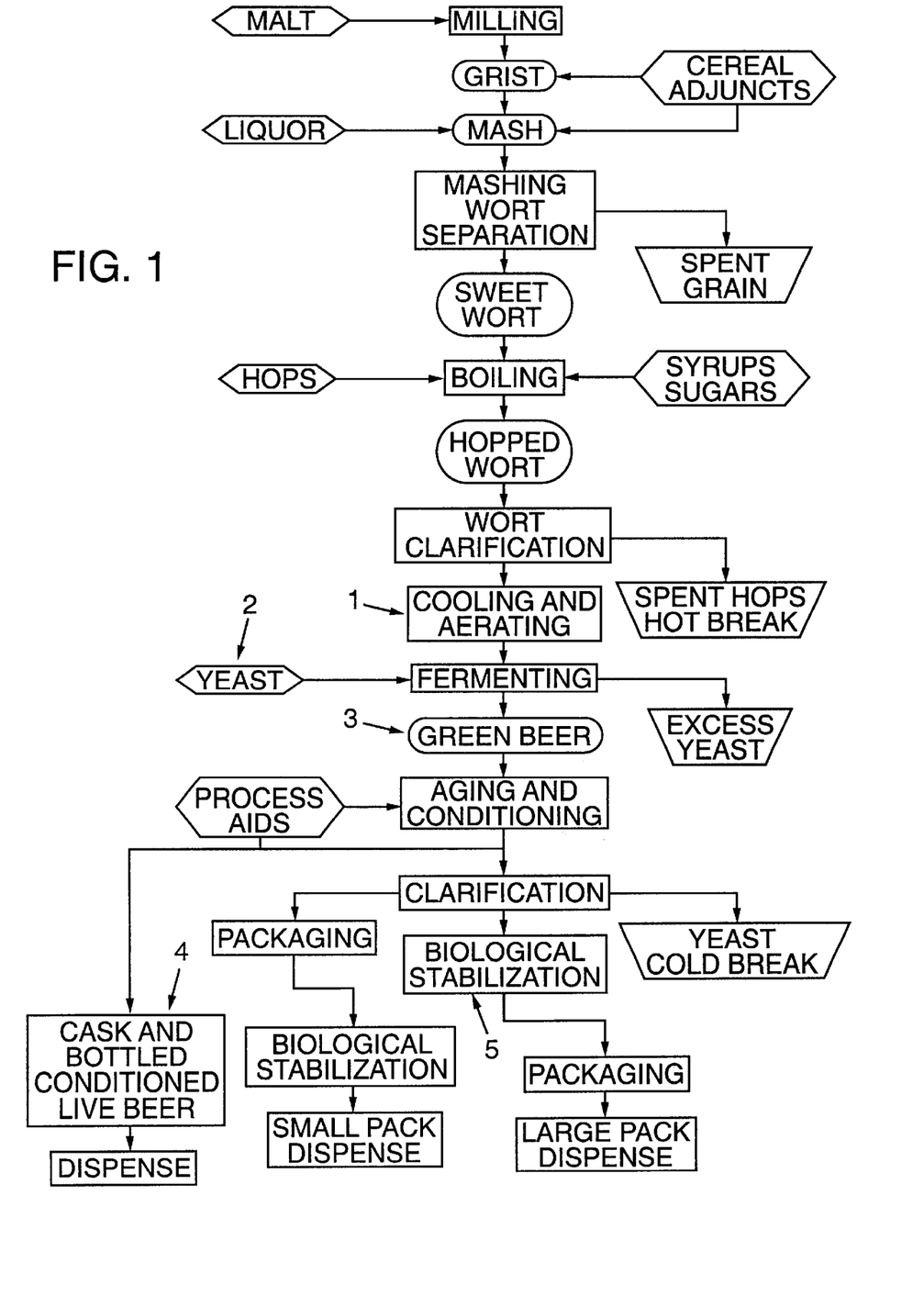
FIG. 1 is a flow diagram of the process for production of beer. Examples of points at which lysozyme can be added to inhibit growth of spoilage bacteria are indicated (numbered "1" to "5").

The beer production process is shown in FIG. 1. Steps during the beer production process at which lysozyme can be added to prevent bacterial growth include, but are not limited to, one or more of the following:

1. Decontamination of Yeast Prior to Fermentation

Lysozyme can be added directly to a yeast inoculum to prevent spoilage of a food product, including beer, wine, liquors, fermented dairy products, etc., by microbes that are lysozyme-sensitive.

Lysozyme can be added to a yeast slurry prior to addition of the yeast slurry to a wort, mash, juice, etc. for fermentation. For production of beer, lysozyme is preferably added to pitching yeast to a concentration of between about 50 ppm and 300 ppm.

Some beer brewers, for example, employ an active dried yeast preparation. The dried yeast can be used as needed, is stable, has high viability, requires no propagation prior to use, and quickly starts fermentation. However, it is economically unfeasible to produce dried yeast preparations under sterile conditions. As a result, the dried yeast invariably is contaminated with microorganisms that can spoil a fermented product, including lactic acid bacteria. Repitching yeast originating from a dried active yeast preparation can be especially problematic, since the proportion of contaminating microorganisms can be higher than in the original dried preparation. This problem can be lessened or eliminated by using a dried yeast preparation that includes sufficient dried lysozyme to inhibit growth of contaminating microorganisms upon rehydration. The dried lysozyme can, for example, be added to the dried yeast prior to packaging for convenient use. Typically, dried yeast preparations are activated prior to use by rehydration in water (e.g., ten times by weight for 30 minutes). Upon rehydration, the concentration of lysozyme in the yeast slurry is preferably about 50 ppm to about 2000 ppm.

For beer production, after the rehydration period, typically one part of a yeast slurry is added to 200 parts of wort to give the proper starting concentration of yeast. For example, if pure lysozyme (pure dried form) is included in the dried yeast preparation at about 0.5% to about 2.0% by weight, upon rehydration in water (ten times by weight) the lysozyme concentration in the yeast slurry would be about 500 ppm to about 2000 ppm, which would be more than a sufficient concentration to eliminate small numbers of contaminating lactic acid bacteria. After addition of the yeast slurry to the wort, the concentration of lysozyme in the wort would be about 2.5 ppm to about 10 ppm.

Pitching yeast is generally reused from one fermentation to another and often becomes contaminated with spoilage bacteria. Current industry practice is to acid wash yeast to selectively eliminate contaminating bacteria, but acid washing is often ineffective and can alter the fermentation performance of the yeast. Lysozyme can be added directly to pitching yeast prior to fermentation to replace acid washing. Alternatively, lysozyme can be added to the yeast prior to or after conventional acid washing treatment to further decontaminate the yeast.

2. Addition to the Wort Prior to Fermentation, e.g., During Cooling

In beer production, for example, a mash is heated to produce a hot wort, which is cooled before addition of yeast to produce a fermentation mixture. As the wort is cooled, it is extremely vulnerable to contamination by spoilage bacteria. Addition of lysozyme to the cooled wort, e.g., at a concentration between about 50 ppm and about 300 ppm, can prevent growth of bacterial contaminants introduced at this stage.

3. During Fermentation

Lysozyme also can be added to the wort after yeast addition, e.g., e.g., at a concentration of between about 50 ppm and about 300 ppm. Doing so prevents lactic acid bacteria introduced previously (e.g., during wort cooling or present in the yeast inoculum) from growing in the fermenting beer.

4,5. During Filling

Lysozyme can be added to the final fermented product itself to prevent spoilage. For example, lysozyme can be added to beer to concentration of between about 5 ppm to about 150 ppm.

Cask- and bottle-conditioned live beers are specialty beers that are neither filtered nor pasteurized, thereby permitting a final carbonation by yeast fermenting in the cask or bottle. Spoilage resulting from bacterial contamination during cask- or bottle-filling operations can be prevented by adding lysozyme prior to or at the time of filling.

Microbrew beers are rarely pasteurized. They are often given a rough filtration to remove yeast, but sterile filtration is usually not performed because it strips away color, mouthfeel, and flavor. Contamination of bottled or kegged beer during filling is a somewhat common problem. Addition of lysozyme at the time of filling provides biological stability to the beer.

Terminology

Unless otherwise noted, terms are to be understood according to conventional usage by those of ordinary skill in the relevant art.

The term "fermented product" includes any product that is produced by a process that includes yeast fermentation. Fermented products include, but are not limited to, malt beverages, wines, liquors, fermented dairy and soy products, etc.

The term "malt beverage" includes alcoholic and nonalcoholic fermented beverages brewed from malt and a cereal grain and optionally flavored with hops, including beers, ales, stouts, porters, lagers, barley wine, etc.

An "effective concentration" of lysozyme is a concentration that is sufficient to inhibit the growth of a bacterium in sample (e.g., a yeast preparation or a fermented product) to a statistically significant degree, preferably by at least about 25%, more preferably by at least about 50%, and most preferably completely inhibiting growth of the bacterium, compared to a control sample lacking lysozyme.

The term "spoilage bacteria" refers to bacterial species that can grow in and are associated with spoilage of a fermented product including, but not limited to, bacteria such as *Lactobacillus brevis, Lactobacillus plantarum, Pediococcus pentosoceus*, etc.

EXAMPLES

Example 1
Stability of Lysozyme Activity in Beer

The realistic shelf life of commercial beer is approximately six months. This experiment was designed to determine whether lysozyme activity is stable after addition to beer over that period of time.

We obtained commercially manufactured beer that was made without hops (made to the formulation of Budweiser®, Anheuser-Busch Co., St. Louis, Mo.). Unhopped beer was selected to allow for a more accurate determination of the influence of lysozyme on flavor and aroma without the sensory contribution of hops. Additionally, since hops have antimicrobial properties, unhopped beer allows for a better assessment of the antimicrobial efficacy of lysozyme.

The beers were opened and lysozyme (Fordras S. A., Lugano, Switzerland) that was solubilized in sterile water was added at the following concentrations: 0, 50, 100, 150, 200, 250, 300, and 400 ppm (each concentration was tested in triplicate). The beers were then immediately recapped. Beer samples were held at both room temperature (21° C.) and under refrigeration (4° C.).

Beer clarity was measured using a nephelometer (turbidimeter) (DRT-100B Research Turbidimeter, HF Scientific, Inc., For Myers, Fla.) calibrated using 0.02 nephelometric turbidity units (NTU) of a certified formazin reference standard (HF Scientific, Inc.) (NTU×25=formazin turbidity units [FTU], which are directly equivalent to ASBC units (hazy, slightly hazy, etc.). Turbidity measurements were made on samples held at room temperature, refrigeration temperature, and on samples that were held under refrigeration and then brought up to room temperature before measuring.

Lysozyme activity in the samples was also measured by the FAO method (Compendium of Food Additive Specifications, FAO Food and Nutrition Paper 52, 1992, pp. 61–64).

Figure 2:
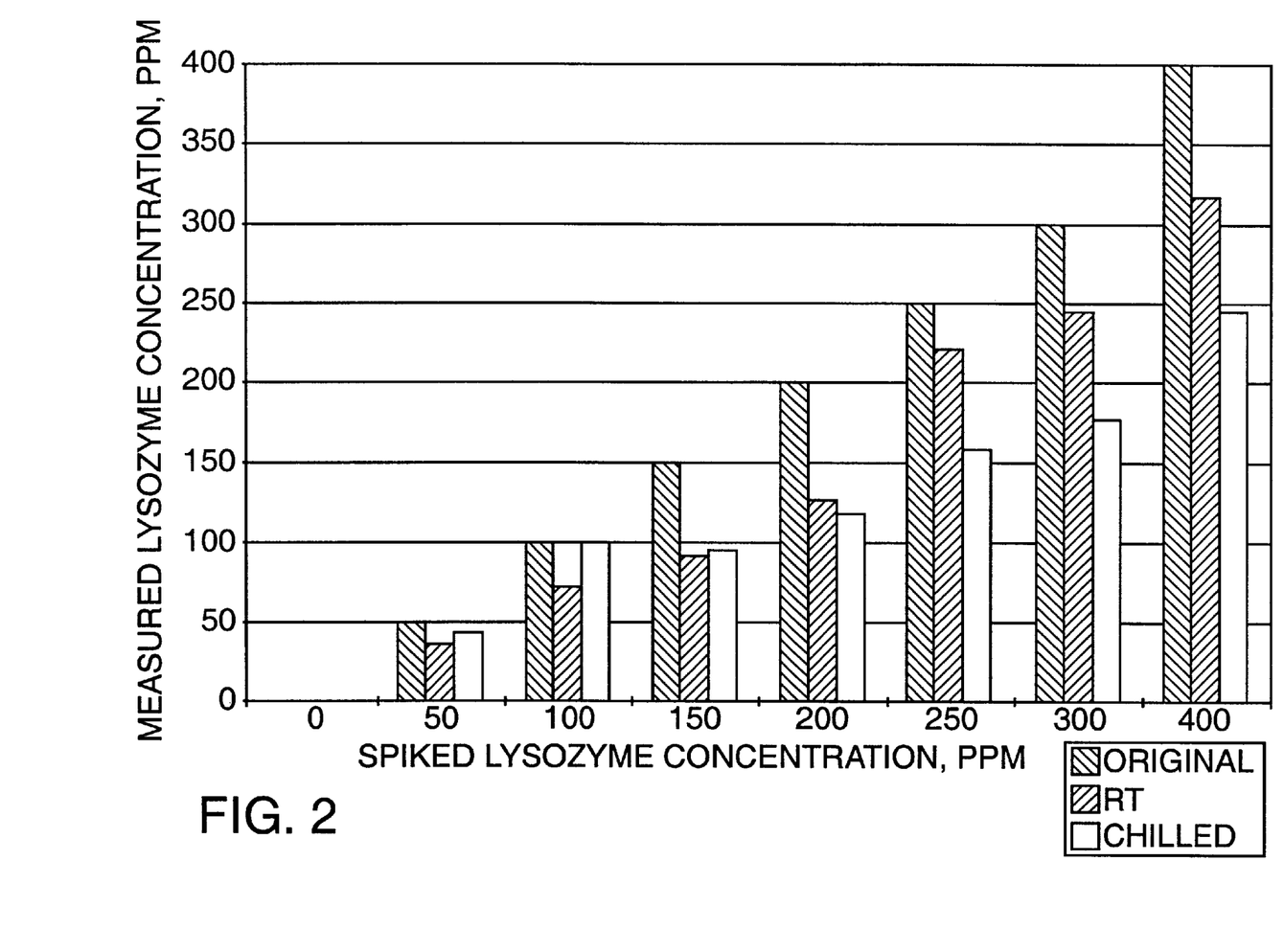
FIG. 2 Is a graph that shows the activity of lysozyme added to beer and held at room temperature (21° C.) or under refrigeration (4° C.) for 194 days.

FIG. 2 shows the measurable activity of lysozyme added to beer and held at room temperature or under refrigeration for 194 days. Losses in lysozyme activity varied from substantially no detectable loss to approximately a 40% loss. There was no statistically significant difference in lysozyme activity if the beer was held at room temperature or at refrigeration temperature. There was also no significant decrease in activity from 60 days storage to 194 days of storage.

Figure 3:
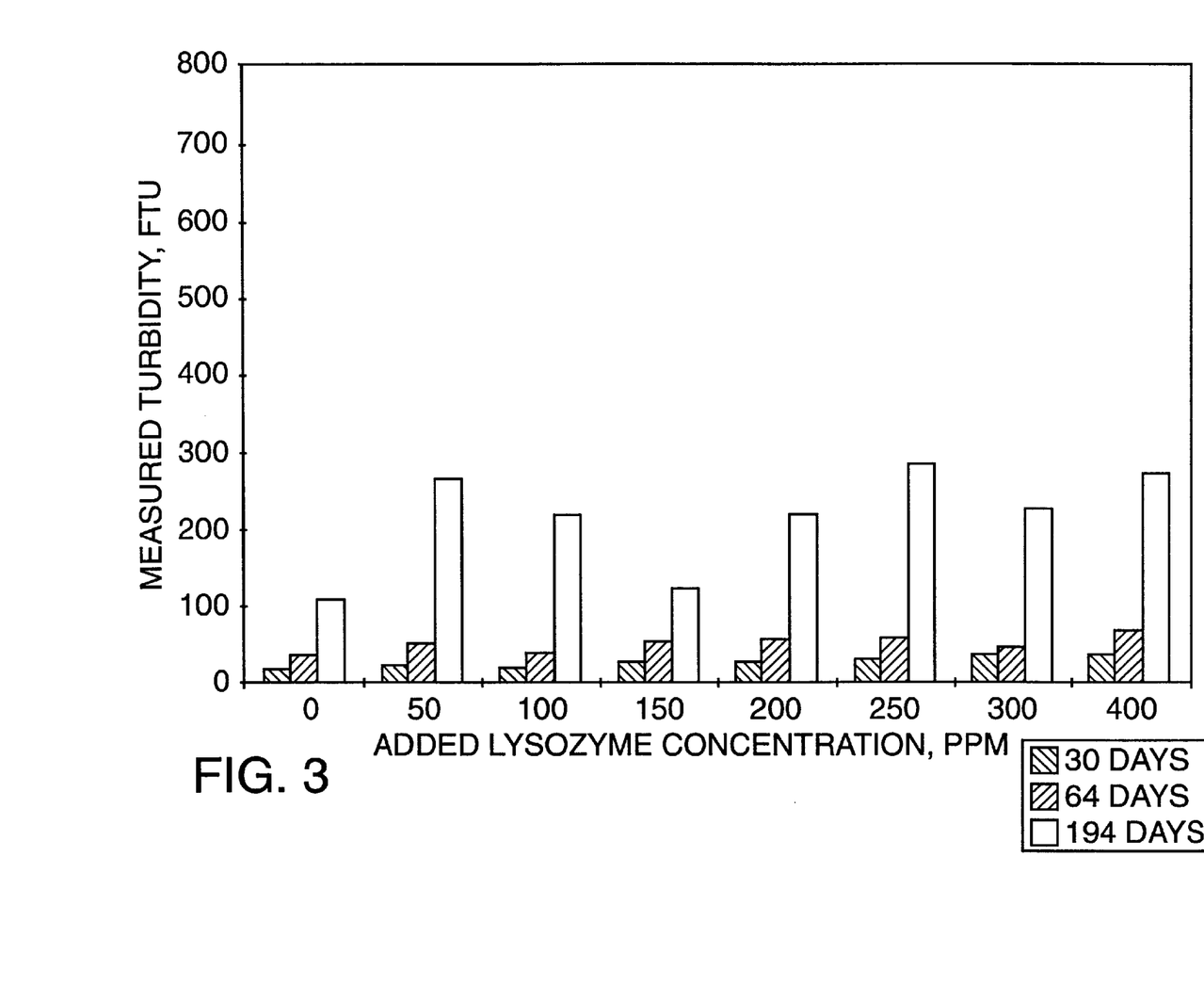
FIG. 3 is a graph that shows the effect of lysozyme on the measured turbidity (FTU) of beer that has been refrigerated (40° C.) for 30, 64, or 194 days.
Figure 4:
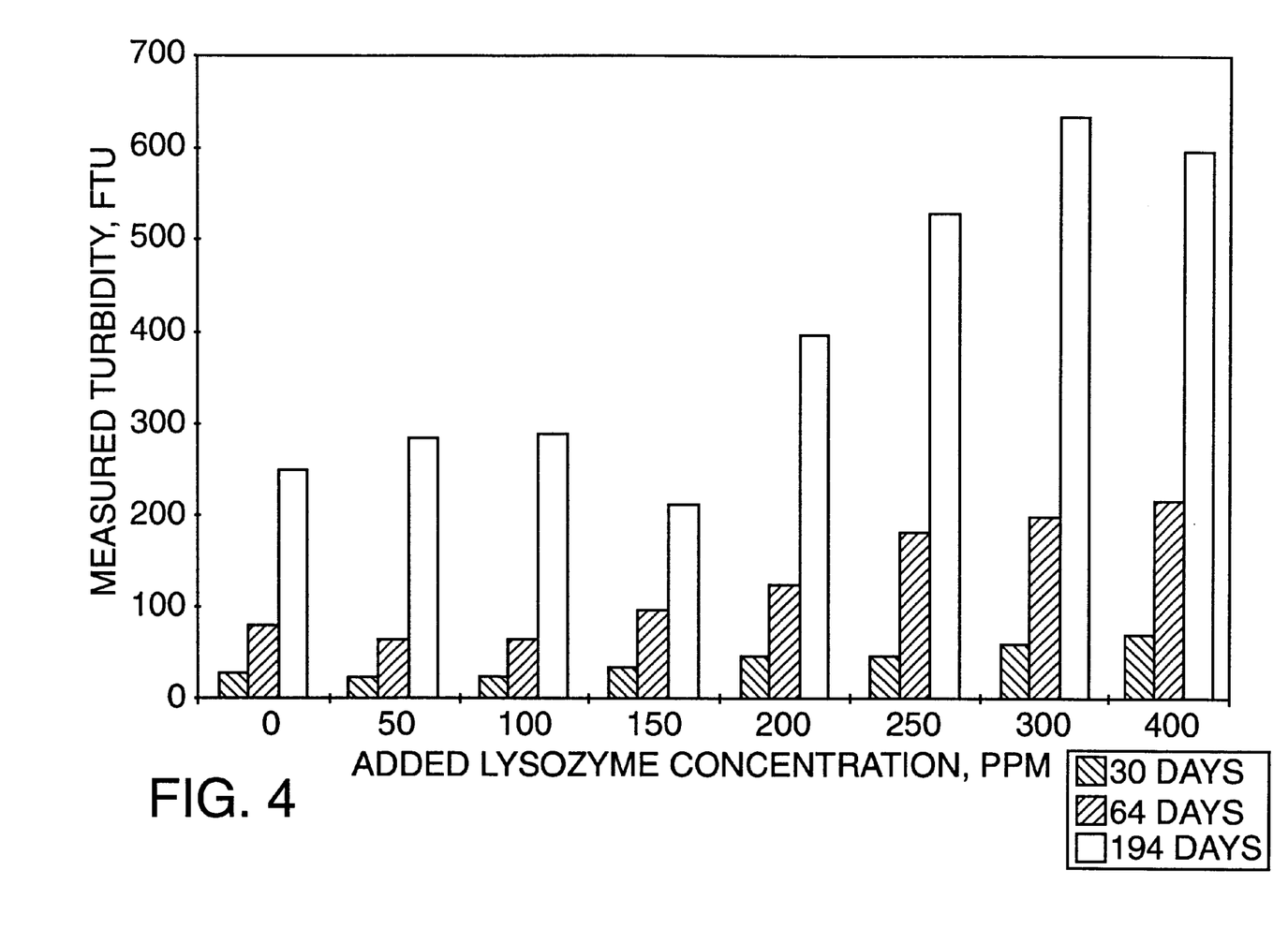
FIG. 4 is a graph that shows the effect of lysozyme on the measured turbidity (FTU) of beer held at room temperature ("RT," 21° C.) for 30, 64, or 194 days.
Figure 5:
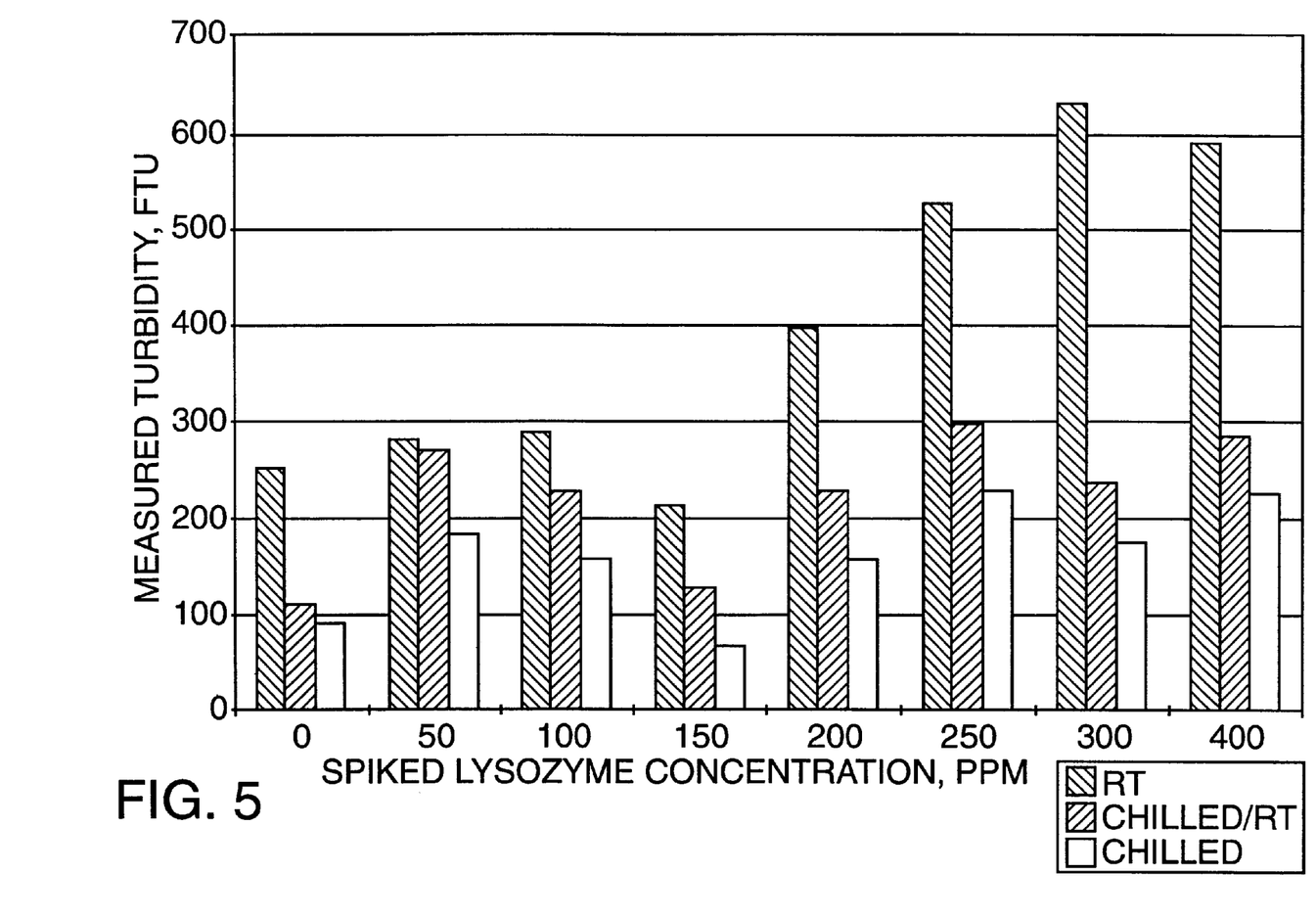
FIG. 5 is a graph that shows the measured turbidity (FTU) at 194 days of beer that has been spiked with lysozyme and held at room temperature ("RT"), chilled (4° C.), or chilled and then brought to room temperature ("chilled/RT").

FIGS. 3, 4, and 5 display the turbidity values of the beer samples stored at room temperature for 30, 64, and 194 days. With beer samples stored at room temperature, there was a general correlation between lysozyme concentration and increased turbidity. Samples held under refrigeration generally had less turbidity than samples held at room temperature, this effect being very pronounced at 194 days. Interestingly, beer samples stored at refrigeration temperature and then brought to room temperature had the least turbidity when compared with other treatments.

Example 2
Evaluation of Lysozyme in Pitching Yeast Contaminated With Lactic Acid Bacteria Amsterdam lager and Nottingham ale yeasts (Lallemond Inc., Montreal, Canada) were cultivated in sterile 7% malt extract (Great Western™ powdered crystal malt) for one week or until fermentation was complete. The yeast were collected, centrifuged, and the yeast cell number was determined. Yeast cultures were diluted to approximately $75 \times 10^6$ cells/mL (seven times the recommended pitching concentration) and the resulting yeast slurries were aliquoted to sterile tubes. Lysozyme was added to the slurries at concentrations of 0, 50, 100, or 200 ppm. *Lactobacillus brevis* (lactic acid bacteria, LAB) was introduced into the yeast slurries at $10^3$ cells/mL ("low" in Table 1) and $10^6$ cells/mL ("high" in Table 1). Selective enumeration of LAB was made with MRS medium (Becton-Dickinson, Cockeysville, Md.) containing 25 mg/L nystatin (Sigma Chemical Co., St. Louis, Mo.) on days 1 and 7 after initial inoculation. Yeast viability and concentration was checked on day 7 after initial inoculation.

Table 1 shows the concentration of *L. brevis* cells (cells/mL) in the slurries at days 1 and 7. Inhibition of *L. brevis* was similar for both Amsterdam lager and Nottingham ale yeasts. There was a slight increase in *L. brevis* growth after 1 day and a substantial increase in growth after 7 days with 0 ppm lysozyme at both starting concentrations of bacteria. There was no bacterial growth with the addition of lysozyme, except for Nottingham ale yeast with 50 ppm lysozyme and $10^6$ bacteria added, in which case the concentration of bacteria dropped to $1.5 \times 10^2$ cells/mL by day 1 but rose to $8.0 \times 10^3$ by day 7, which is less than the amount in the sample lacking lysozyme.

TABLE 1

| Lysozyme (ppm) | 0 | 50 | 100 | 200 |
|---|---|---|---|---|
| Nottingham Ale Yeast | | | | |
| Day 1-low | $6.4 \times 10^3$ | 0 | 0 | 0 |
| Day 7-low | $5.0 \times 10^6$ | 0 | 0 | 0 |
| Day 1-high | $5.8 \times 10^6$ | $1.5 \times 10^2$ | 0 | 0 |
| Day 7-high | $7.8 \times 10^7$ | $7.9 \times 10^3$ | 0 | 0 |
| Amsterdam Lager Yeast | | | | |
| Day 1-low | $3.0 \times 10^5$ | 0 | 0 | 0 |
| Day 7-low | $5.0 \times 10^6$ | 0 | 0 | 0 |
| Day 1-high | $2.7 \times 10^7$ | 0 | 0 | 0 |
| Day 7-high | $7.9 \times 10^7$ | 0 | 0 | 0 |

When checked on day 7, yeast viability and concentration remained the same as when the yeast slurries originally were inoculated with lysozyme indicating that the lysozyme had no apparent effect on the yeast.

Example 3
Effect of Lysozyme on Beer Foam Stability

Figure 6:
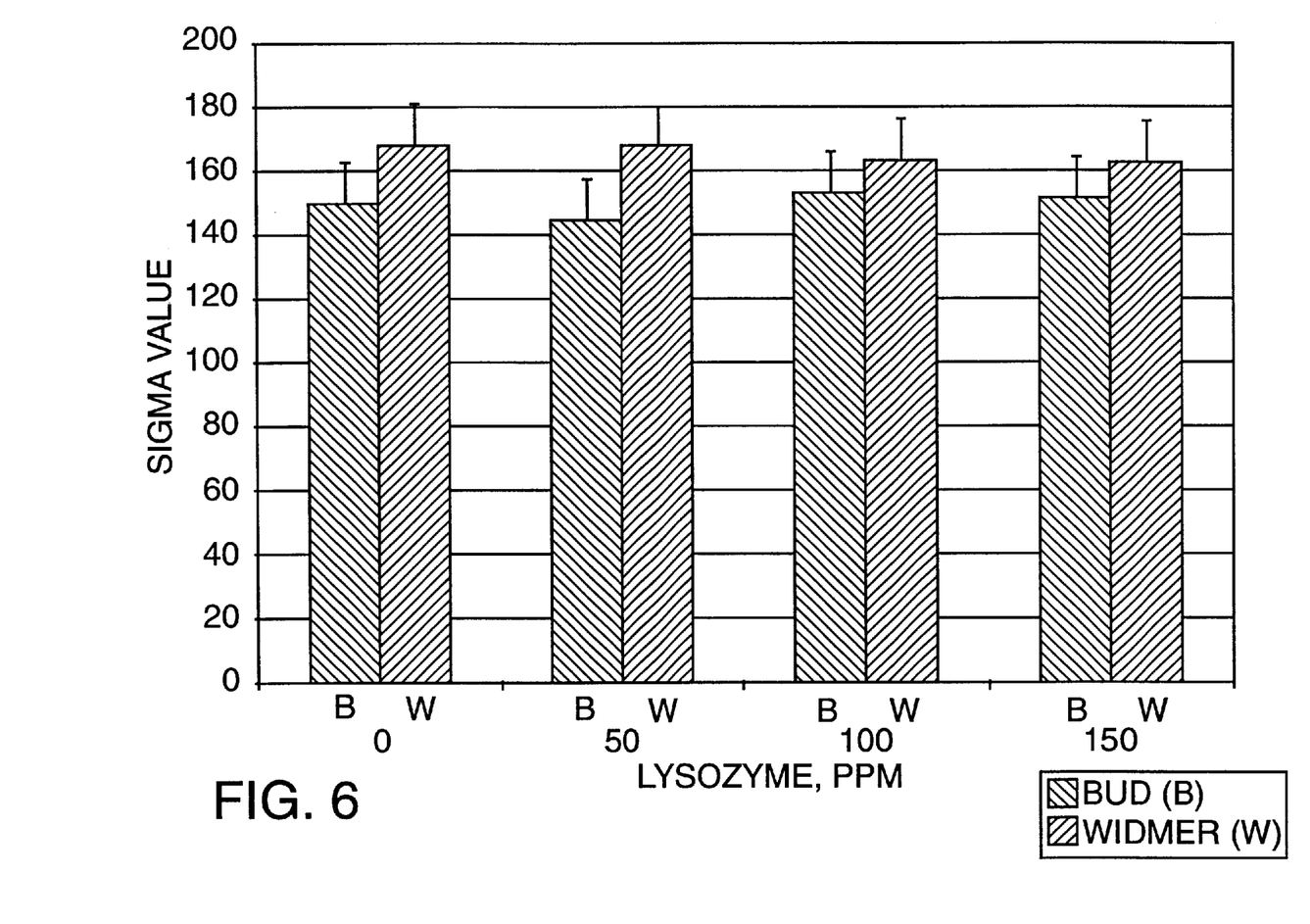
FIG. 6 is a graph that shows the stability of bear foam one week after the beer has been treated with lysozyme. B, Budweiser® beer; W, Widmer® Hefeweisen beer.

Three replicates each of Budweiser® (Anheuser-Busch, St. Louis, Mo.) and of Widmer® Hefeweisen beer (Portland, Oreg.) were treated with 0, 50, 100, or 150 ppm lysozyme. Foam stability (foam collapse rate in Sigma units) was tested after one week by the Sigma value method (*Quality Control Course Laboratory Exercises*, Siebel institute of Technology, Chicago, Ill.). [Another standard method for testing foam stability is described by the American Society of Brewing Chemists (ASBC), in "Foam Collapse Rate" (Beer 22) *Standard Methods of Analysis* (issued 1992).] As shown in FIG. 6, there was no significant difference (2-factor ANOVA without replication) among the treatments with differing concentrations of lysozyme for either beer.

A slight decrease in beer brilliance was observed visually in Budweiser® beer treated with lysozyme, although an actual precipitation was not observed (a decrease in brilliance could not be observed in the Widmer® Hefeweizen beer, since precipitation is normally present in this unfiltered beer).

Example 4
Stability of Lysozyme Activity in Wine

Lysozyme was added to red wine (Pinot noir, made from grapes obtained from Oregon State University by standard winemaking procedures) to a concentration of 0, 100, 200, or 300 ppm. Water-extracted freeze-dried oak tannins (Food, Wine and Spirit Group, Inc., P.O. Box 10234, Napa, Calif.) and held at room temperature. Samples were tested in duplicate. At various periods of time after addition of lysozyme and oak tannins, the lysozyme concentration of the wine samples and the total phenolics as gallic acid equivalents (GAE) were measured.

Table 2 shows the lysozyme concentration of the wine samples after 7 days at room temperature. For samples that had no oak tannins, lysozyme concentration was approximately 50% of the original concentration. For samples with 100 ppm oak tannins, the lysozyme concentration was less than 30% of the original concentration. For samples with 200 ppm oak tannins, the lysozyme concentration was less than 20% of the original concentration. For samples with 300 ppm oak tannins, the lysozyme concentration was 1.5% or less of the original concentration.

Table 3 shows the lysozyme concentration of the wine samples after 28 days (four weeks) at room temperature. For samples that had no oak tannins, lysozyme concentrations were approximately 30% of the original concentration. For samples with 100 ppm oak tannins, the lysozyme concentration had fallen to less than 20% of the original concentration. For samples with 200 ppm oak tannins, the lysozyme concentration was less than 15% of the original concentration. For samples with 300 ppm oak tannins, the lysozyme concentration was 1.0% or less of the original concentration.

Table 4 shows the lysozyme concentration of the wine samples after 84 days (twelve weeks) at room temperature. For samples that had no oak tannins, lysozyme concentrations were approximately 20% of the original concentration. For samples with 100 ppm oak tannins, the lysozyme concentration had fallen to less than 7% of the original concentration. For samples with 200 ppm oak tannins, the lysozyme concentration was less than 4% of the original concentration. For samples with 300 ppm oak tannins, the lysozyme concentration had fallen to undetectable levels.

Tables 5–7 show levels of phenolics (GAE) after 7, 28, and 84 days, respectively. There was no significant difference in the amount of GAE detected in samples that had been spiked with oak tannins. Addition of one gram of the oak tannin preparation (600–650 mg of GAE) added to wine at 100 ppm should increase the GAE by 65. A straightforward correlation between added tannins and GAE was not observed.

In summary, while the measured concentrations of lysozyme decreased over time in red wine, the addition of oak tannins to the wine markedly enhanced the decrease in measured lysozyme concentrations. The decrease in lysozyme activity was inversely proportionate to the increase in oak tannin concentration. In addition, samples containing lower lysozyme concentrations were affected much more severely. The amount of oak tannins added made no apparent difference in the amount of GAE detected.

TABLE 2

Measurement of Lysozyme Concentration in Wine with Oak Tannins (1 Week)

| Oak Tannins (ppm) | Spiked Lysozyme Concentration (ppm) | | | |
|---|---|---|---|---|
| | 0 | 100 | 200 | 300 |
| 0 | 0 | 27.4 | 77.4 | 156.8 |
| 100 | 0 | 1.8 | 44.5 | 94.6 |
| 200 | 0 | 0 | 21.2 | 59.4 |
| 300 | 0 | 0 | 1.8 | 4.1 |

TABLE 3

Measurement of Lysozyme Concentration in Wine with Oak Tannins (4 Weeks)

| Oak Tannins (ppm) | Spiked Lysozyme Concentration (ppm) | | | |
|---|---|---|---|---|
| | 0 | 100 | 200 | 300 |
| 0 | 0 | 15.3 | 56.7 | 114.5 |
| 100 | 0 | 1.3 | 30.1 | 69.5 |
| 200 | 0 | 0 | 6.25 | 43.9 |
| 300 | 0 | 0 | 0.7 | 1.82 |

TABLE 4

Measurement of Lysozyme Concentration in Wine with Oak Tannins (12 Weeks)

| Oak Tannins (ppm) | Spiked Lysozyme Concentration (ppm) | | | |
|---|---|---|---|---|
| | 0 | 100 | 200 | 300 |
| 0 | 0 | 7.7 | 38.0 | 83.0 |
| 100 | 0 | 0 | 12.2 | 18.0 |
| 200 | 0 | 0 | 1.84 | 11.4 |
| 300 | 0 | 0 | 0 | 0 |

TABLE 5

Measured Phenol Concentration (GAE) in Wine with Added Lysozyme and Oak Tannins (1 week)

| Original Lysozyme Concentration (ppm) | Spiked Oak Tannin Conc. (ppm) | | | |
|---|---|---|---|---|
| | 0 | 100 | 200 | 300 |
| 0 | 0 | 7.7 | 38.0 | 83.0 |
| 100 | 0 | 0 | 12.2 | 18.0 |
| 200 | 0 | 0 | 1.84 | 11.4 |
| 300 | 0 | 0 | 0 | 0 |

TABLE 6

Measured Phenol Concentration (GAE) in Wine
with Added Lysozyme and Oak Tannins (4 weeks)

| Original Lysozyme | Spiked Oak Tannin Conc. (ppm) | | | |
|---|---|---|---|---|
| Concentration (ppm) | 0 | 100 | 200 | 300 |
| 0 | 850 | 799 | 961 | 995 |
| 100 | 934 | 777 | 906 | 908 |
| 200 | 825 | 837 | 866 | 880 |
| 300 | 800 | 802 | 867 | 844 |

TABLE 7

Measured Phenol Concentration (GAE) in Wine
with Added Lysozyzme and Oak Tannins (12 weeks)

| Original Lysozyme | Spiked Oak Tannin Conc. (ppm) | | | |
|---|---|---|---|---|
| Concentration (ppm) | 0 | 100 | 200 | 300 |
| 0 | 985 | 1043 | 1205 | 1179 |
| 100 | 1032 | 777 | 1145 | 996 |
| 200 | 974 | 1055 | 1107 | 1159 |
| 300 | 854 | 880 | 1062 | 1240 |

Example 5
Sensitivity of Various Spoilage Bacteria to Lysozyme

Figure 7:
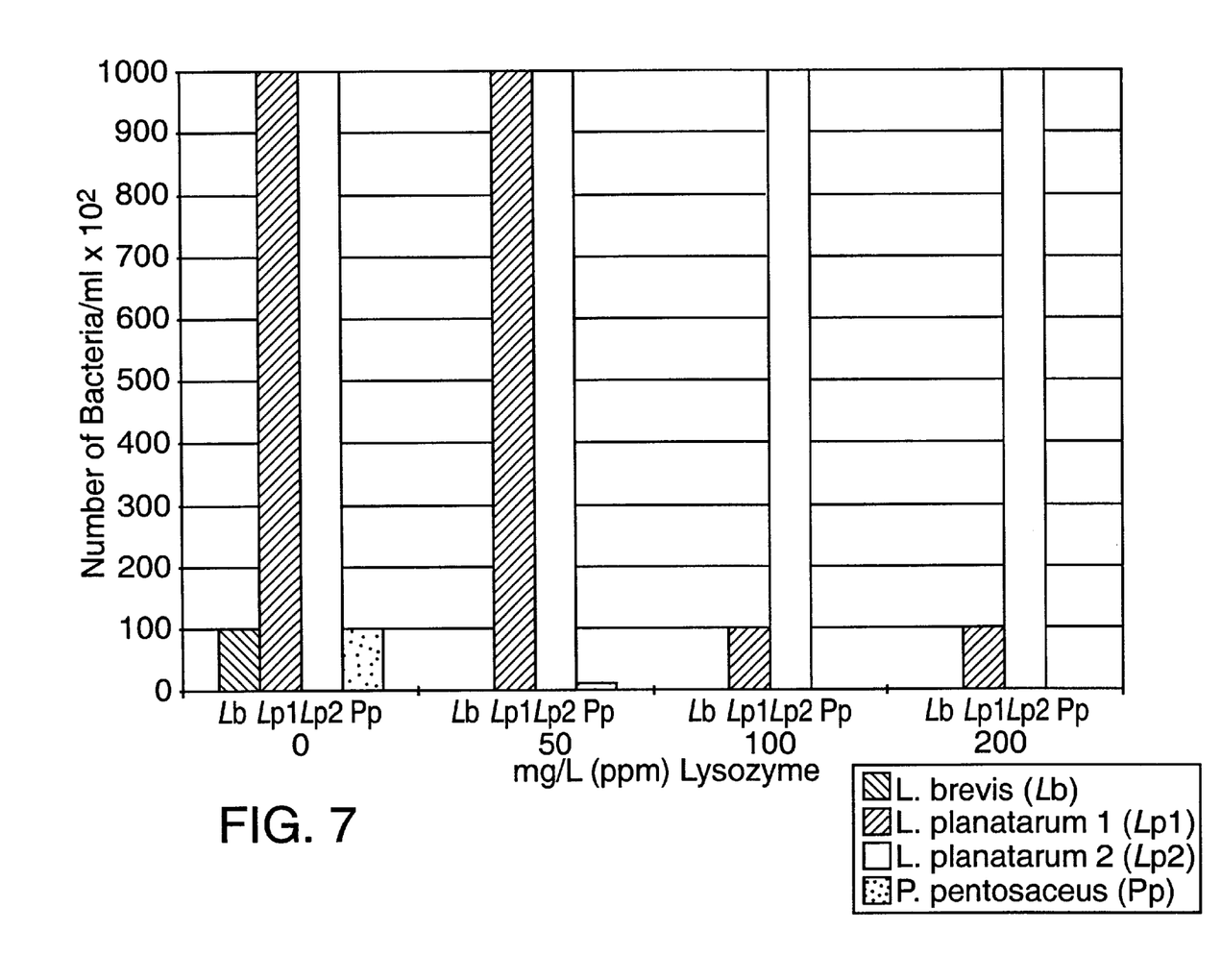
FIG. 7 is a graph showing the effect of lysozyme on lactic acid bacteria in pitching yeast (original concentration of bacteria=$10^3$/mL) by day 7. Lb, *Lactobacterium brevis*; Lp1, *Lactobacterium plantarum* strain 1; Lp2, *Lactobacterium plantarum* strain 2; Pp, *Pediococcus pentosaceus*.
Figure 8:
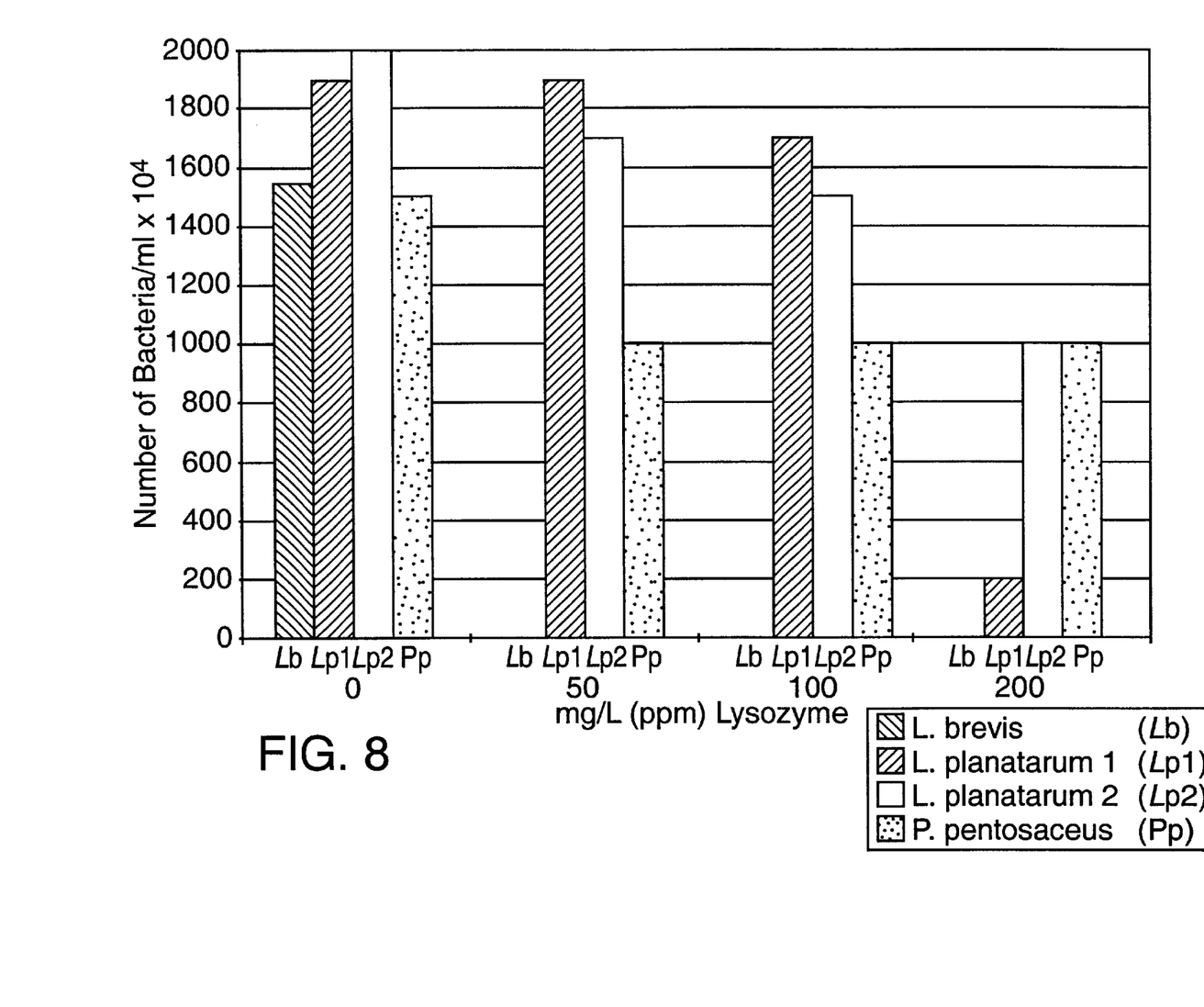
FIG. 8 is a graph showing the effect of lysozyme on lactic acid bacteria in pitching yeast (original concentration of bacteria=$10^6$/mL) by day 7. Lb, *Lactobacterium brevis*; Lp1, *Lactobacterium plantarum* strain 1; Lp2, *Lactobacterium plantarum* strain 2; Pp, *Pediococcus pentosaceus*

Various strains of spoilage bacteria were investigated to determine their sensitivity to the antimicrobial effects of lysozyme, in particular one strain of *Lactobacterium brevis*; two different strains of *Lactobacterium plantarum*, and one strain of *Pediococcus pentosaceus*. Amsterdam lager and Nottingham ale yeast were cultivated in sterile 7% malt extract broth for one week or until fermentation was complete. The yeast cells were collected, centrifuged and enumerated. Yeast cultures were diluted to approximately $75 \times 10^6$ cells/mL and distributed to sterile tubes. Lysozyme was added at concentrations of 0, 50, 100, and 200 ppm (mg/L). The spoilage bacteria strains discussed below were introduced to the yeast slurries at concentrations of $5 \times 10^3$ cells/mL and $5 \times 10^6$ cells/mL. Selective enumeration of the strain of spoilage bacteria was made with MRS medium containing 25 mg/L nystatin on days one and seven after initial inoculation. Yeast viability and concentration were checked on day seven after initial inoculation. The results are shown in FIG. 7 (original concentration of bacteria=$10^3$/mL) and FIG. 8 (original concentration of bacteria=$10^6$/mL).

Figure 9:
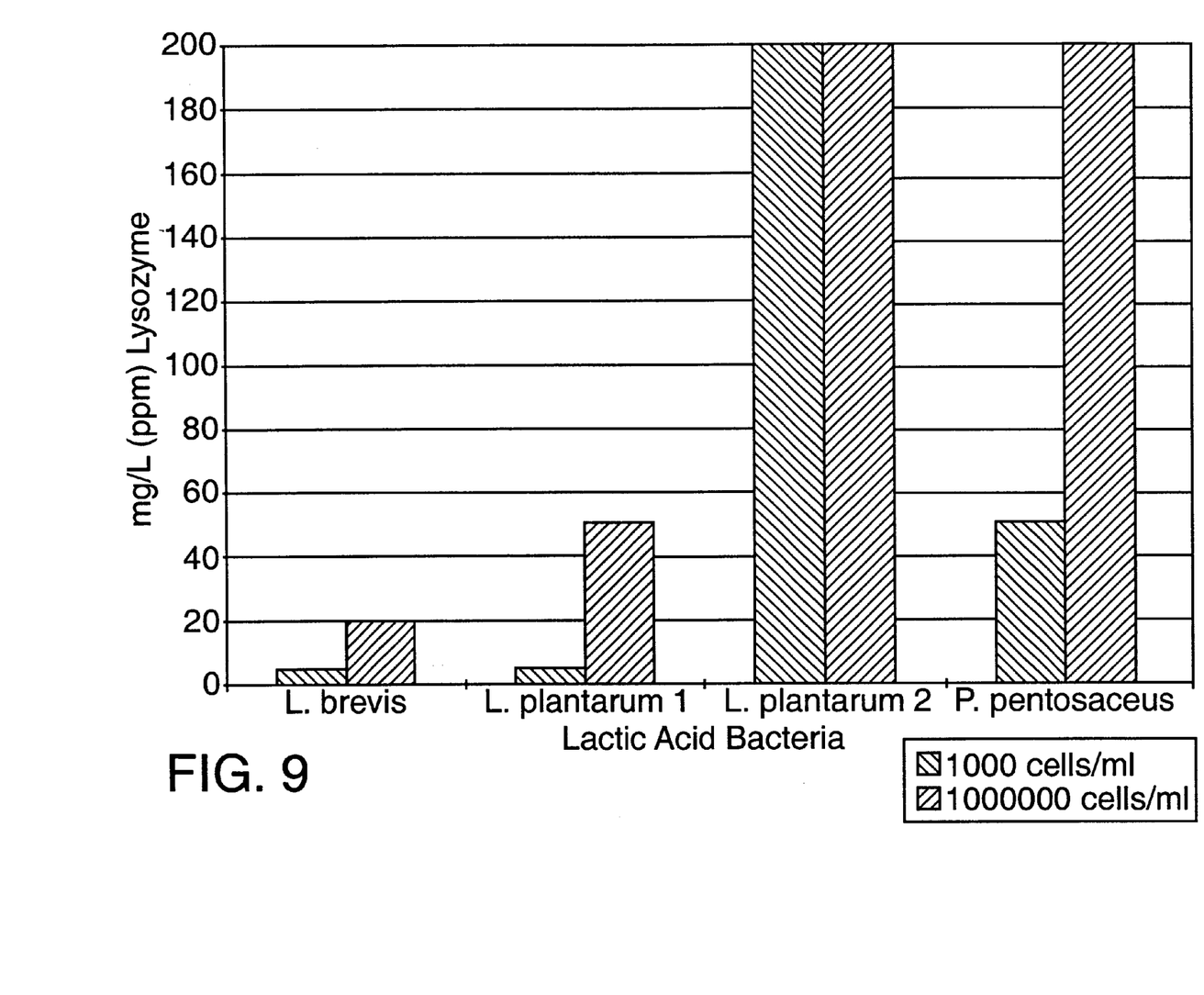
FIG. 9 is a graph showing the minimum inhibitory concentration (MIC) of lysozyme on lactic acid bacteria in pitching yeast. For each bacterial strain, the original concentration of bacteria is $10^3$/mL (left) or $10^6$/mL (right).

In order to determine the minimum inhibitory concentration of lysozyme for each strain of spoilage bacteria tested, cells of the strain were inoculated into sterile nutrient broth at $10^3$ and $10^6$ cells/mL. Lysozyme resuspended in sterile water was added at concentrations from 0–100 mg/L (ppm) Each concentration of lysozyme was tested in duplicate. Once inoculated, tubes were incubated at 32° C. Samples (100 μL) from each tube were plated onto MRS agar at days one and seven post-inoculation. The first concentration demonstrating no growth for both replicates at both sampling points was determined to be the minimum inhibitory concentration (MIC). The results are shown in FIG. 9.

A. Effect of Lysozyme on *Lactobacillus brevis*

When inoculated with the Amsterdam lager yeast, both concentrations of *L. brevis* showed a large increase in growth after one day and displayed very little change in concentration when tested at seven days with 0 ppm lysozyme. There was no growth in any of the tubes containing lysozyme at either day one or day seven.

When inoculated with the Nottingham ale yeast, both concentrations of *L. brevis* showed virtually no increase in growth after one day and substantial growth when tested at day seven with 0 ppm lysozyme. Growth was also observed at day one in the tube containing 50 ppm lysozyme and inoculated with $10^6$ bacteria per mL, although the concentration was significantly less than the original inoculum. By day seven, the concentration of bacteria in this tube had increased somewhat, although it was still significantly less than the original inoculum. Growth of *L. brevis* in the sample containing 50 ppm lysozyme was consistently less than in the sample containing 0 ppm lysozyme.

Yeast viability and concentration, which were checked on day seven, remained the same as when originally inoculated. This indicates that the added lysozyme had no effect on the yeast.

The MIC for *L. brevis* at $10^3$ cells/mL in nutrient broth was 5 mg/L (ppm) lysozyme. The MIC for *L. brevis* at $10^6$ cells/ml in nutrient broth was 20 mg/L (ppm) lysozyme.

Both high ($10^6$/mL) and low ($10^3$/mL) concentrations of this strain of *L. brevis* were sensitive to even low levels of lysozyme.

B. Effect of Lysozyme on *Lactobacillus plantarum* #1

When inoculated with Amsterdam lager yeast, both concentrations of *L. plantarum* #1 showed a large increase in growth after one day and had no change in concentration when tested at seven days with 0 ppm lysozyme. There was slight growth at all concentrations of lysozyme after one day with more substantial growth occurring after seven days for the low concentration of bacteria. Growth was slightly less or the same as that seen in the samples with no lysozyme added, but more than the original concentration of bacteria added. For the higher concentration of bacteria, there was substantial growth at day one and no change in bacterial concentration when tested at seven days.

When inoculated with Nottingham ale yeast, both concentrations of *L. plantarum* #1 showed a large increase in growth after one day and no change in concentration when tested at seven days with 0 ppm lysozyme. However, there was slightly more growth for the lower concentration of bacteria. For the higher concentration of bacteria, substantial growth occurred by day one at all lysozyme concentrations but growth dropped off significantly by day seven.

Yeast viability and concentration on day seven remained the same as when originally inoculated, indicating that the added lysozyme had no effect on the yeast.

The MIC for *L. plantarum* #1 was 5 mg/L (ppm) lysozyme at $10^3$ cells/mL in nutrient broth and 50 mg/L (ppm) lysozyme at $10^6$ cells/mL.

*L. plantarum* #1 was partially resistant to lysozyme. Both high ($10^6$/mL) and low ($10^3$/mL) concentrations of bacteria were resistant to lysozyme when yeast were also present in the culture. When yeast were not present in the culture, low concentrations of bacteria ($10^3$/mL) were sensitive to lysozyme, while high concentrations of bacteria ($10^6$/mL) were only partially sensitive.

C. Effect of Lysozyme on *Lactobacillus plantarum* #2

When inoculated with the Amsterdam lager yeast, both concentrations of *L. plantarum* #2 showed a large increase in growth after one day and had no change in concentration when tested at 7 days with 0 ppm lysozyme. There was slight growth at all concentrations of lysozyme after one day, with more substantial growth occurring after seven days for the low concentration of bacteria. The growth was slightly less or the same as that seen in the samples with no lysozyme added but more than the original concentration of bacteria added. For the higher concentration of bacteria, there was substantial growth at day one and no change in bacterial concentration when tested at seven days. The bacterial growth diminished in inverse proportion to the concentration of lysozyme, however bacterial growth was not eliminated.

When inoculated with the Nottingham ale yeast, both concentrations of L. plantarum #2 again showed a large increase in growth after one day and had no change in concentration when tested at day seven with 0 ppm lysozyme. However, there was slightly more growth than the 0 ppm lysozyme sample at day seven for the lower concentration of bacteria. For the higher concentration of bacteria, substantial growth occurred by day one at all lysozyme concentrations, and dropped off significantly by day seven.

Yeast viability and concentration, which were checked on day seven, remained the same as when originally inoculated. This indicates that the added lysozyme had no effect on the yeast.

The MIC for L. plantarum #2 at both $10^3$ cells/mL and $10^6$ cells/mL in nutrient broth was >200 mg/L (ppm) lysozyme.

This strain of bacteria was resistant to treatment with lysozyme. Both high ($10^6$/mL) and low ($10^3$/mL) concentrations of bacteria were found to be resistant to even low levels of lysozyme. Bacterial growth decreased in inverse proportion to the concentration of lysozyme, but was not eliminated. Bacterial resistance to lysozyme seemed to be greater in the presence of yeast.

D. Effect of Lysozyme on *Pediococcus pentosaceus*

No differences were observed for *P. pentosaceus* when inoculated with the Amsterdam lager versus the Nottingham ale yeast. When inoculated with either the Amsterdam lager or the Nottingham ale yeast, both concentrations of *P. pentosaceus* showed a large increase in growth after one day that remained constant when tested at day seven with 0 ppm lysozyme. Growth was also observed at day one in all tubes containing lysozyme (50, 100, 200 ppm) that were originally inoculated with $10^6$ bacteria/mL. This concentration remained constant when tested on day seven. Tubes containing lysozyme that were originally inoculated with $10^3$ bacteria/mL did not show growth at day one. By day 7, however, bacterial growth was observed in the $10^3$/mL tube containing 50 ppm lysozyme, while there was no growth in the tubes contained 100 and 200 ppm lysozyme. Growth in samples containing lysozyme was slightly less than in samples with 0 ppm lysozyme.

Yeast viability and concentration when checked on day 7 remained the same as when originally inoculated. This indicates that the added lysozyme had no effect on the yeast.

The MIC for this strain of *P. pentosaceus* was 50 mg/L (ppm) lysozyme at $10^3$ cells/mL in nutrient broth and >200 mg/L (ppm) at $10^6$ cells/mL.

This strain of *Pediococcus pentosaceus* was only partially sensitive to lysozyme. High concentrations ($10^6$/mL) of cells were particularly resistant to lysozyme treatment, although low concentration ($10^3$/mL) of cells were also resistant to some levels of lysozyme. Resistance to lysozyme appeared to be slightly greater in the presence of yeast.

E. Conclusions

*Lactobacillus brevis* was the most sensitive of the bacteria tested. One strain of *Lactobacillus plantarum* was found to be completely resistant under the conditions of this study, while another strain of *L. plantarum* was found to be sensitive to fairly low levels of lysozyme. A *Pediococcus pentosaceus* strain exhibited moderate resistance to the effects of lysozyme. All bacteria tested were more resistant to lysozyme treatment when in the presence of yeast, possibly because the yeast adsorbed some of the lysozyme. The sensitivity of a particular strain of bacteria to the effects of lysozyme was heavily dependent upon the type of medium that was used. Bacteria that were sensitive to lysozyme treatment in nutrient broth were resistant to the same levels of lysozyme when grown in MRS broth.

Having illustrated and described the principles of the present invention, it should be apparent to persons skilled in the art that the invention can be modified in arrangement and detail without departing from such principles. We claim all modifications that are within the spirit and scope of the appended claims.

What is claimed is:

1. A method of making a fermented product comprising:
providing a first wort that comprises a fermentable carbohydrate;
adding a yeast preparation to the first wort;
providing conditions that are conducive to fermentation of the carbohydrate by the yeast preparation, thereby producing a first fermented mixture;
separating yeast from the first fermented mixture to provide a volume of a fermented beverage;
preparing a re-pitching inoculum comprising at least a portion of the yeast separated from the first fermented mixture;
adding to the re-pitching inoculum an amount of lysozyme effective to inhibit growth of a bacterium in the re-pitching inoculum without acid washing the re-pitching inoculum, thereby generating a lysozyme-containing re-pitching inoculum mixture that has not been acid washed;
adding the lysozyme-containing non-acid washed inoculum mixture to a second wort, the second wort comprising a fermentable carbohydrate; and
providing conditions that are conducive to fermentation of the carbohydrate of the inoculated second wort by the yeast of the lysozyme-containing non-acid washed inoculum mixture, thereby producing a second fermented mixture.

2. The method of claim 1 further comprising adding to the lysozyme-containing non-acid washed inoculum mixture a compound that causes greater inhibition of growth of the bacterium by the lysozyme.

3. The method of claim 2 wherein the compound is selected from the group consisting of a chelating agent, butyl p-hydroxybenzoate, a p-hydroxy-benzoic ester, β-glycopyranose aerodehydrogenase, an amino acid, hydrogen peroxide, an organic acid, and a mixture thereof.

4. The method of claim 1 wherein the yeast preparation that is added to the first wort is a dried yeast preparation that comprises an active dried yeast and an amount of dried lysozyme that is effective to inhibit growth of a bacterium in the yeast preparation upon rehydration.

5. The method of claim 4 further comprising adding an aqueous liquid to the yeast preparation that is added to the first wort to produce a rehydrated yeast preparation, wherein adding the yeast preparation to the first wort comprises adding the rehydrated yeast preparation to the first wort, the amount of the lysozyme in the dried yeast preparation being an amount that is effective to inhibit growth of the bacterium in the rehydrated yeast preparation.

6. The method of claim 4 wherein the dried yeast preparation comprises about 0.5% to about 2.0% dried lysozyme by weight.

7. The method of claim 1 wherein the amount of lysozyme added to the re-pitching inoculum is between about 50 ppm and about 2000 ppm.

* * * * *